US011369291B2

(12) United States Patent
Huang et al.

(10) Patent No.: US 11,369,291 B2
(45) Date of Patent: Jun. 28, 2022

(54) PHYSIOLOGICAL SIGNAL MONITORING DEVICE AND SENSOR HOLDER THEREOF

(71) Applicant: BIONIME CORPORATION, Taichung (TW)

(72) Inventors: Chun-Mu Huang, Taichung (TW); Chieh-Hsing Chen, Taichung (TW)

(73) Assignee: BIONIME CORPORATION, Taichung (TW)

( * ) Notice: Subject to any disclaimer, the term of this patent is extended or adjusted under 35 U.S.C. 154(b) by 0 days.

(21) Appl. No.: 16/945,661

(22) Filed: Jul. 31, 2020

(65) Prior Publication Data

US 2021/0030337 A1    Feb. 4, 2021

Related U.S. Application Data

(60) Provisional application No. 62/882,140, filed on Aug. 2, 2019.

(51) Int. Cl.
*A61B 5/145* (2006.01)
*A61B 5/00* (2006.01)
(Continued)

(52) U.S. Cl.
CPC ........ *A61B 5/14503* (2013.01); *A61B 5/0002* (2013.01); *A61B 5/0004* (2013.01); (Continued)

(58) Field of Classification Search
CPC . A61B 5/0002; A61B 5/0004; A61B 5/14503; A61B 5/1451; A61B 5/14532; A61B 5/14546; A61B 5/14865; A61B 5/150748; A61B 5/150847; A61B 5/6801; A61B 5/6833; A61B 5/68335; A61B 5/6848; A61B 5/6867; A61B 5/688; A61B 2560/045; A61B 2560/063; A61B 2562/0295; A61B 2562/14; A61B 2562/16; A61B 2562/166; A61B 2562/168;
(Continued)

(56) References Cited

U.S. PATENT DOCUMENTS 9,357,951 B2    6/2016   Simpson et al.
9,693,713 B2    7/2017   Pace et al.
(Continued)

FOREIGN PATENT DOCUMENTS

JP    2018000310 A    1/2018

OTHER PUBLICATIONS

European Search Report dated Oct. 1, 2020 cited in application EP 20 18 9181.

*Primary Examiner* — Allen Porter
*Assistant Examiner* — Abid A Mustansir
(74) *Attorney, Agent, or Firm* — Perkins Coie LLP; Viola Kung

(57) ABSTRACT

The present invention discloses a holder carrying thereon a sensor to measure a physiological signal of an analyte in a biological fluid, wherein the sensor has a signal detection end and a signal output end, and the holder includes an implantation hole being a channel for implanting therethrough the sensor and containing a part of the sensor, and a containing indentation containing the signal output end, wherein the containing indentation has a surrounding wall kept apart from the signal output end to define a space.

8 Claims, 16 Drawing Sheets

(51) Int. Cl.
*A61M 5/315* (2006.01)
*A61M 5/32* (2006.01)
*H01R 12/73* (2011.01)

(52) U.S. Cl.
CPC ...... *A61B 5/14532* (2013.01); *A61B 5/14546* (2013.01); *A61B 5/6801* (2013.01); *A61B 5/688* (2013.01); *A61B 5/6867* (2013.01); *A61M 5/31513* (2013.01); *A61M 5/31571* (2013.01); *A61M 5/3287* (2013.01); *A61B 5/1451* (2013.01); *A61B 2560/045* (2013.01); *A61B 2562/0295* (2013.01); *A61B 2562/14* (2013.01); *A61B 2562/16* (2013.01); *A61B 2562/166* (2013.01); *A61B 2562/168* (2013.01); *A61B 2562/225* (2013.01); *A61B 2562/226* (2013.01); *A61B 2562/227* (2013.01); *A61M 2205/3327* (2013.01); *H01R 12/737* (2013.01)

(58) Field of Classification Search
CPC ........ A61B 2562/225; A61B 2562/226; A61B 2562/227; A61B 2562/242; A61B 5/1486; A61M 5/31513; A61M 5/31571; A61M 5/3287; A61M 2205/3327; H01R 12/737
See application file for complete search history.

(56) References Cited

U.S. PATENT DOCUMENTS

| | | |
|---|---|---|
| 10,413,224 B2 | 9/2019 | Vang |
| 2008/0234563 A1* | 9/2008 | Regittnig ........... A61B 5/14532 600/365 |
| 2012/0197098 A1 | 8/2012 | Donnay et al. |
| 2017/0188910 A1 | 7/2017 | Halac et al. |
| 2017/0188912 A1 | 7/2017 | Halac et al. |
| 2017/0340280 A1* | 11/2017 | Lu ........................ A61B 5/6838 |
| 2018/0317820 A1 | 11/2018 | Pace et al. |

* cited by examiner

PHYSIOLOGICAL SIGNAL MONITORING DEVICE AND SENSOR HOLDER THEREOF

CROSS-REFERENCE TO RELATED APPLICATION AND CLAIM OF PRIORITY

This application claims priority to U.S. Provisional Patent Application No. 62/882,140, filed Aug. 2, 2019, which is incorporated herein in its entirety by reference.

FIELD OF THE INVENTION

The present invention is related to a physiological signal monitoring device. In particular, the present invention is related to a thin physiological signal monitoring device.

BACKGROUND OF THE INVENTION

Patients with chronic conditions (such as diabetes and chronic cardiovascular disease) need to routinely monitor changes in the data of certain physiological parameters (such as concentrations of blood glucose, blood lipid and cholesterol, or other parameters) so as to control the condition effectively and avoid deterioration of their condition and get timely treatment.

However, a lot of physiological data has to be obtained via invasive methods. In addition, in order to effectively monitor the changes in the physiological parameters, it is necessary to acquire multiple measurements every day. Taking blood glucose measurement as an example, a traditional blood glucose measurement is usually performed by using a test strip and a glucose meter, and the level of the blood glucose is obtained by measuring the magnitude of current generated by the reaction between the glucose in the blood and glucose oxidase in the test strip. This measuring method requires patients to collect blood from their fingertips every day and drip blood onto the test strip to obtain a single blood glucose data. When patients need to obtain multiple measurements, they must experience the discomfort of repeated blood collections. In addition, for patients with unstable blood glucose level, it is insufficient to use the instantaneous blood glucose value as an accurate medication basis for doctors.

In order to avoid patients' discomfort due to multiple blood draws or body fluid extractions, some skilled in the art tend to use small sensing elements implanted in the subcutaneous tissue for a relatively long time, to match reusable signal processing components having signal processing capabilities. Since there is no need to remove this sensing element every day, and data such as blood glucose, blood lipid and cholesterol concentrations or other data for physiological parameters can be collected and analyzed at any time, real-time physiological data monitoring can be provided. Therefore, there is a need for a thin physiological signal monitoring device that can be implanted under the skin for a long time.

SUMMARY OF THE INVENTION

The present invention provides a physiological signal monitoring device suitable for implantation under the skin for a long time, which can monitor the patient's physiological data in real time.

The present invention discloses a physiological signal monitoring device for implantation under a skin of a living body to measure a physiological signal of an analyte in a biological fluid from the living body, and the physiological signal monitoring device includes: a sensor having a signal detection end and a signal output end, a transmitter having a port connected to the signal output end and receiving the physiological signal, and a holder carrying thereon the sensor, wherein the signal detection end is to be implanted under the skin to detect the physiological signal, and the signal output end is to output the physiological signal. The holder includes an implantation hole being a channel for implanting therethrough the sensor and containing a part of the sensor and a containing indentation containing the signal output end, wherein the containing indentation has a surrounding wall kept apart from the signal output end to define a space such that the port is received within the space of the containing indentation, and the signal output end is electrically connected to the port.

The present invention further discloses a holder carrying thereon a sensor to measure a physiological signal of an analyte in a biological fluid, wherein the sensor has a signal detection end and a signal output end, and the holder includes an implantation hole being a channel for implanting therethrough the sensor and containing a part of the sensor, and a containing indentation containing the signal output end, wherein the containing indentation has a surrounding wall kept apart from the signal output end to define a space.

The present invention further discloses a holder carrying thereon a sensor to measure a physiological signal of an analyte in a biological fluid, wherein the sensor has a signal detection end and a signal output end, and the holder includes an implantation hole being a channel for implanting therethrough the sensor and containing a part of the sensor, a containing indentation containing the signal output end, wherein the containing indentation has a surrounding wall kept apart from the signal output end to define a space, a waterproof seal disposed above the implantation hole, and an elastic divider disposed in the implantation hole to separate the implantation hole and covering all over a cross-sectional area of the implantation hole.

The physiological signal monitoring device of the present invention achieves the purpose of thinness and detachability by the complementary structural design between the transmitter and the holder, prevents external liquid from flowing into the device and prevents blood from leaking through the implantation site by the waterproof sealing effect of elastic body. At the same time, the physiological signal monitoring device of the present invention enables the sensor to be more stably carried on the holder through the limiting and fixing means of the filler, the limiter and the blocking element.

BRIEF DESCRIPTION OF THE DRAWINGS

The objectives and advantages of the present invention will become more readily apparent to those ordinarily skilled in the art after reviewing the following detailed descriptions and accompanying drawings.

DETAILED DESCRIPTION OF THE PREFERRED EMBODIMENTS

The present invention will now be described more specifically with reference to the following embodiments. It is to be noted that the following descriptions of the preferred embodiments of this invention are presented herein for purpose of illustration and description only; they are not intended to be exhaustive or to be limited to the precise form disclosed.

The physiological signal monitoring device of the present invention is used to measure the physiological signals of an analyte in a biological fluid. The term "biological fluid" as used herein refers the biological fluid such as blood, interstitial fluid, cerebrospinal fluid, lymphatic fluid, etc.

The term "analyte" as used herein refers to substances from the above biological fluid that can reflect the physiological state of a living body, including but not limited to sugar, protein, lipid, cholesterol, vitamins and cytokines, or other substances present in the biological fluid. The term "biological signal" as used herein refers to the amount or concentration of the analyte above. In one embodiment, the physiological signal is the glucose concentration in the human body, preferably the glucose concentration in the interstitial fluid. In some embodiments, the physiological signals may be also constituted by content or concentration of metabolites, antigens, antibodies, etc. that naturally occur in the body fluids or are endogenous. Alternatively, the physiological signal may also be the content or concentration of the substance introduced into the body or the exogenous substance, for example, the concentration of the chemical agent, drug, pharmaceutical composition, or metabolite of the pharmaceutical composition. In one embodiment, the exogenous substance may be insulin or glucagon.

Figure 1:
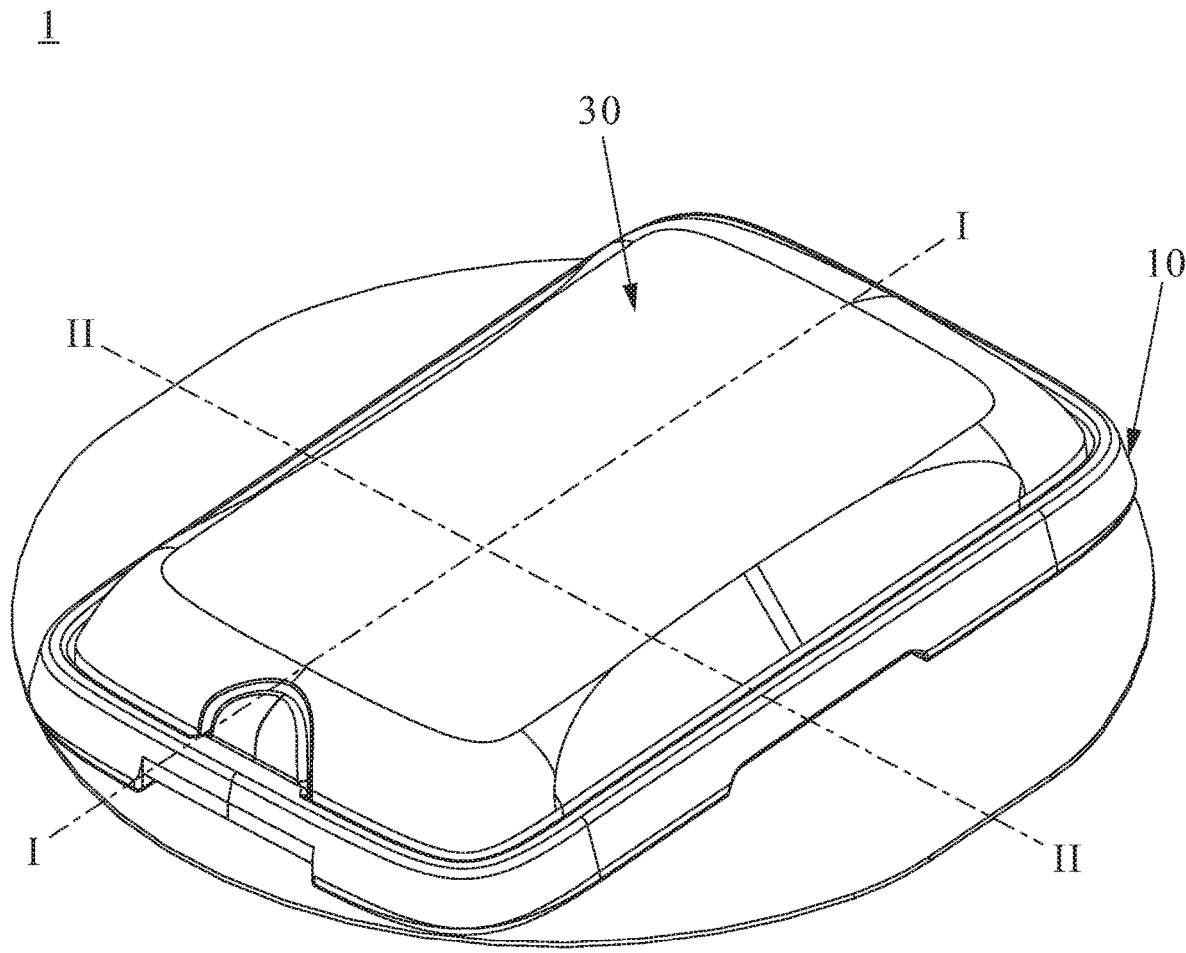
FIG. 1 is a perspective view of the physiological signal monitoring device in the present invention.

Please refer to FIG. 1, which is a perspective view of the physiological signal monitoring device 1 in the present invention. The physiological signal monitoring device 1 of the present invention includes a base 10, a holder 20 (not shown), a transmitter 30 and a sensor 40 (not shown). The base 10 can be fixed on the skin surface of a living body (such as a human body), the sensor 40 is fixed in the holder 20, the holder 20 can be combined with the base 10, and the transmitter 30 is detachably disposed on the holder 20.

Figure 2A:
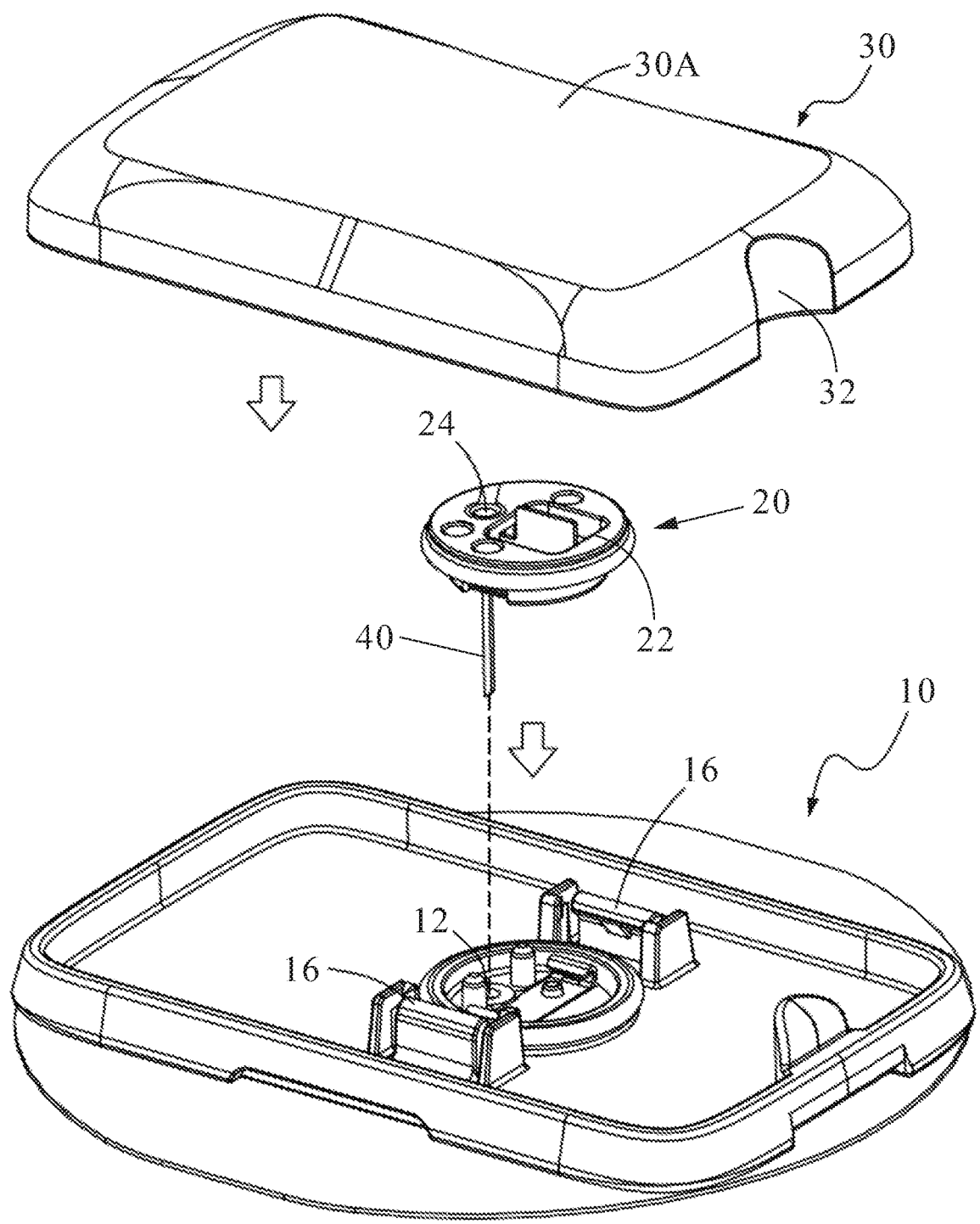
FIG. 2A is an exploded perspective view of the physiological signal monitoring device in the present invention.

Please refer to FIG. 2A, which is an exploded perspective view of the physiological signal monitoring device 1 in the present invention. The corresponding positions among the base 10, the holder 20 carrying a sensor 40 and the transmitter 30 can be seen from the Figure. When the user installs the physiological signal monitoring device 1, the base 10 is first fixed on the skin surface, and the holder 20 is engaged with the base 10 by an additional implanting device (not shown) to implant the sensor 40 under the skin. After the implanting device is removed, the holder 20 is combined with the base 10 fixed to the skin surface of the user. The transmitter 30 is covered on the base 10 and electrically connected to the sensor 40, to receive the physiological signal from the sensor 40 and transmit it to an external device. In order to show the direction in which the transmitter 30 is combined with the base 10, an upper surface 30A of the transmitter 30 is shown in FIG. 2A.

Figure 2B:
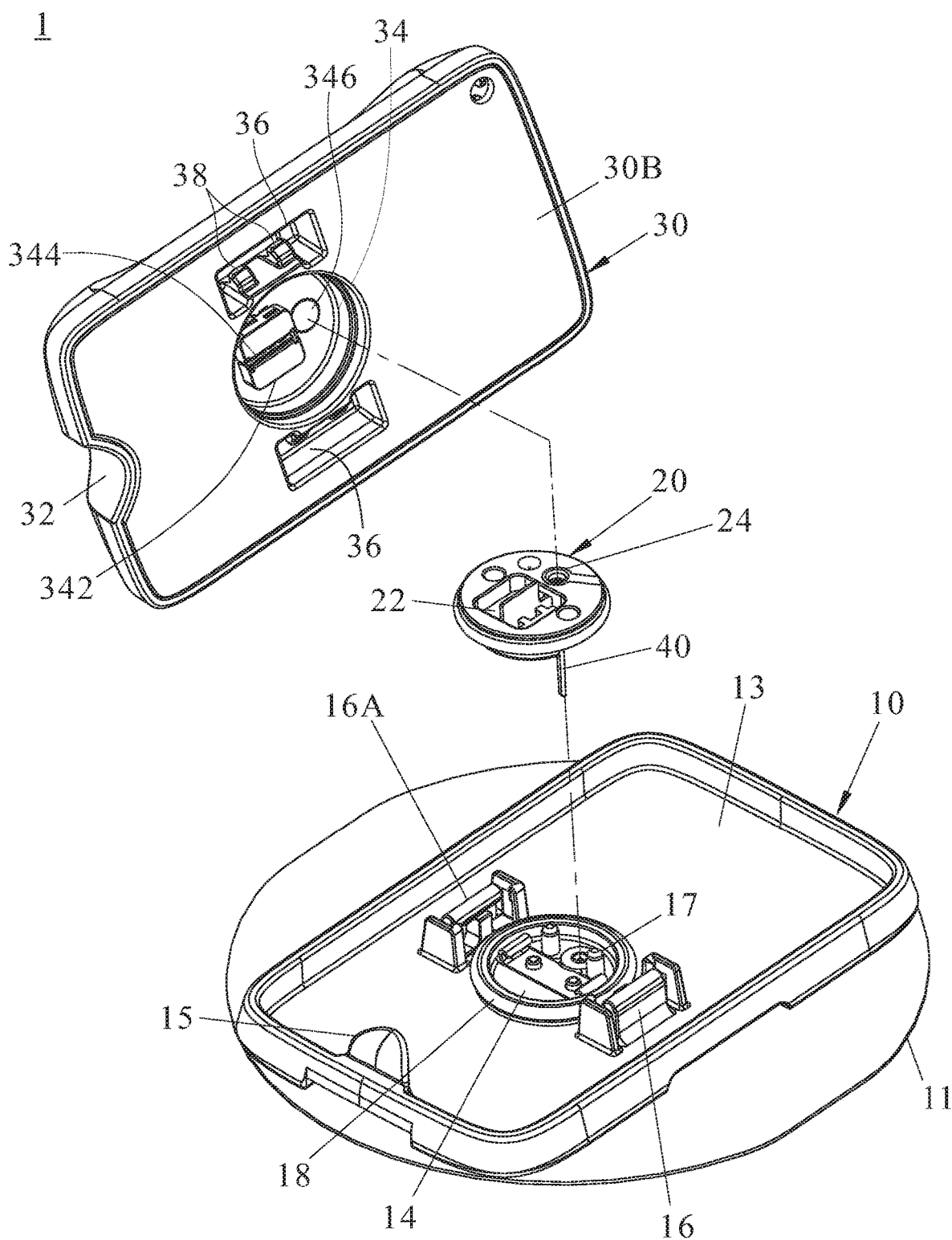
FIG. 2B is another exploded perspective view of the physiological signal monitoring device in the present invention.

Please refer to FIG. 2B, which is another exploded perspective view of the physiological signal monitoring device 1 in the present invention. In order to more clearly understand the corresponding structures among the base 10, the holder 20 and the transmitter 30, a lower surface 30B of the transmitter 30 is shown in FIG. 2B. The lower surface 30B of the transmitter 30 is provided with a first open portion 34 and a pair of second open portions 36, wherein the first open portion 34 is used to accommodate the holder 20 and the accommodating portion 14 of the base 10, and the second open portions 36 are used to contain a pair of first engaging members 16 of the base 10. A second engaging member 38 is provided inside each second open portion 36 to correspond to the first engaging members 16. When the transmitter 30 is combined with the base 10, the second engaging member 38 of each second open portion 36 is engaged with its corresponding first engaging member 16. The components in each main structure will be described in sequence in the following.

Figure 7A:
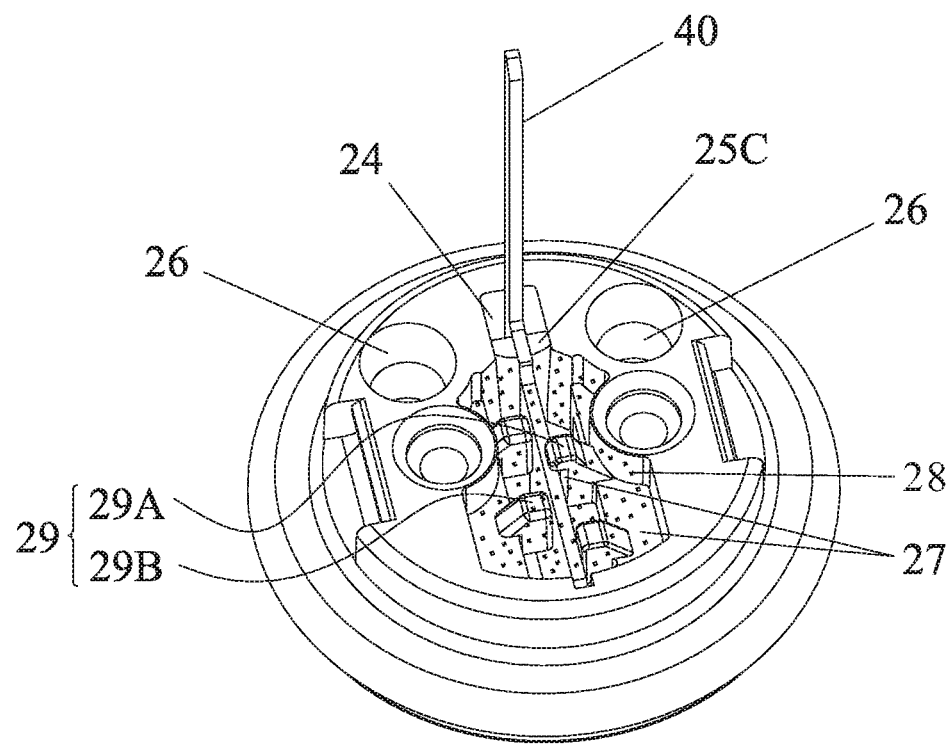
FIG. 7A is another perspective view of the holder of the physiological signal monitoring device in the present invention.
Figure 7B:
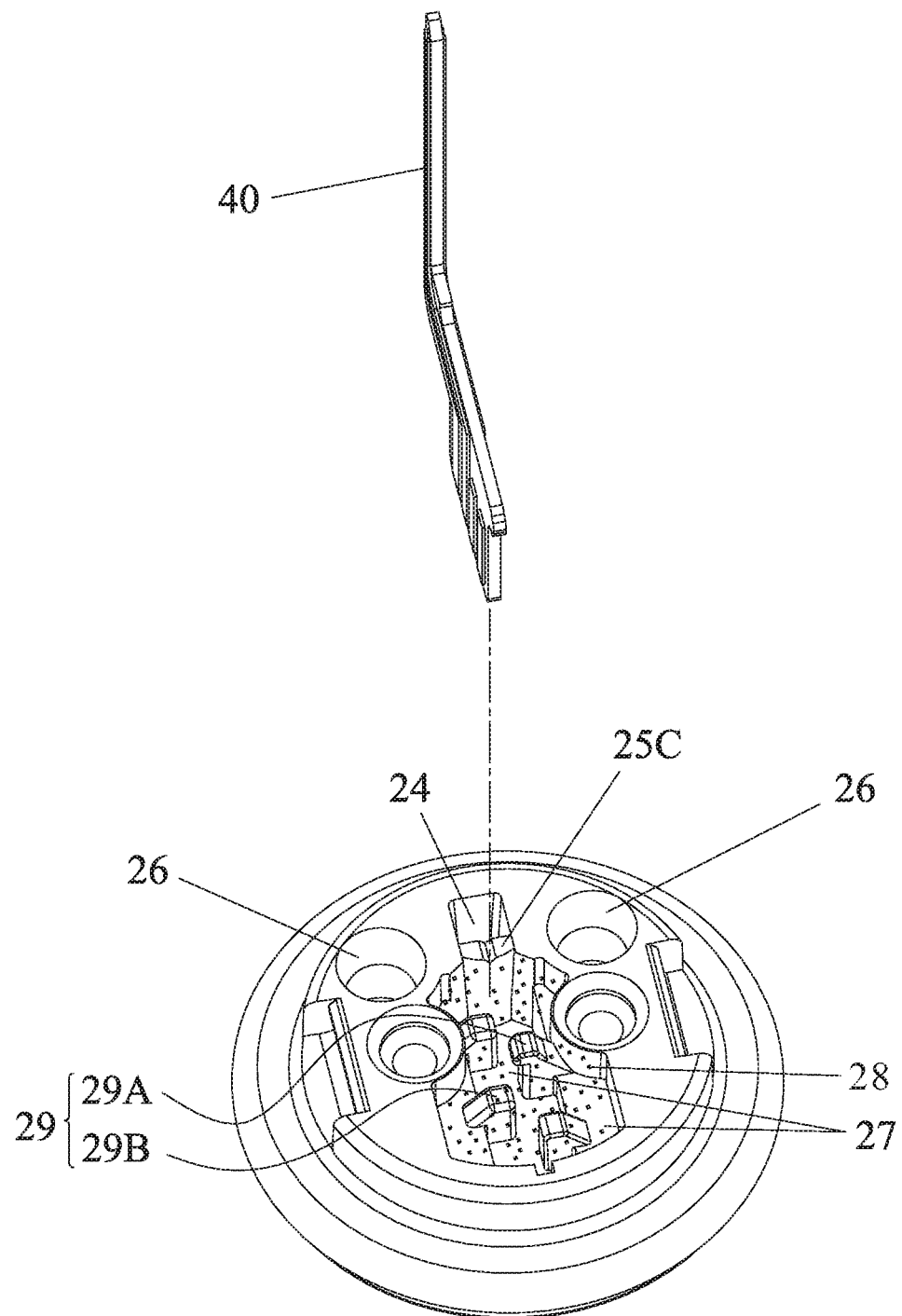
FIG. 7B is an exploded perspective view of FIG. 7A.

Please continue to refer to FIG. 2A and FIG. 2B for the detailed description of the base 10. The base 10 includes a patch 11, a through-hole 12, a base body 13, the accommodating portion 14, a first fool-proof portion 15, a pair of first engaging members 16, two positioning pillars 17 and a first elastic body 18. The patch 11 is disposed on the bottom surface of the base 10 and is used to adhere to the skin surface of the living body. A waterproof material is included in the patch 11 to prevent unclean liquid from penetrating through the patch 11 and contacting the wound, thereby the risk of wound infection is avoided. The through-hole 12 is provided with the accommodating portion 14 therethrough for implanting the signal detection end 44 of the sensor 40 under the skin of living body. The accommodating portion 14 is used to accommodate the holder 20. The base body 13 has a peripheral portion corresponding to the shape of the edge of the transmitter 30. The first fool-proof portion 15 is disposed on the peripheral portion of the base body 13 to correspond to a second fool-proof portion 32 on the transmitter 30 when the transmitter 30 is placed on the base 10. With the aid of the first fool-proof portion 15 and the second fool-proof portion 32, the user can easily identify the installation orientation of the transmitter 30 and that of the base 10 when he or she attaches the latter transmitter 30 onto the former base 10. The pair of first engaging members 16 are protrudingly provided on the top surface of the base body 13, and each first engaging member 16 corresponds to the second open portion 36 on the transmitter 30 for engaging with the bottom of the transmitter 30. When the holder 20 is combined to the base 10, the two positioning pillars 17 are accommodated in the positioning holes 26 at the bottom of the holder 20 (as shown in FIGS. 7A and 7B), and the first elastic body 18 is disposed on the edge of the accommodating portion 14 to forms an interference fit with the holder 20, thereby limiting and fixing the holder 20 to the base 10.

As shown in FIG. 2B, each first engaging member 16 includes an engaging portion 16A. Each engaging portion 16A corresponds to the second engaging member 38 in the second open portion 36 of the transmitter 30. When the engaging portions 16A are pushed against by an external force, each engaging portions 16A rotates away from the respective second engaging member 38, so as to separate the first engaging members 16 from the second engaging members 38.

The first elastic body 18 is disposed on the accommodating portion 14 on the top surface of the base 10, and is made of an elastic material and formed with the base body 13 by double injection molding so as to form an interference fit with the holder 20 made by a harder material. In one embodiment, the first elastic body 18 is circularly disposed on the accommodating portion 14 to form a concave slot for containing the holder 20. Preferably, the first elastic body 18 is formed on the inner surface, the outer surface, and the top surface of the peripheral wall of the accommodating portion 14. In another embodiment, the first elastic body 18 is dispersedly disposed on the accommodating portion 14 to define a fixation area for containing the holder 20 in this fixation area. Preferably, the first elastic body 18 is dispersedly arranged on the inner surface, the outer surface and the top surface of the peripheral wall of the accommodating portion 14.

Figure 3:
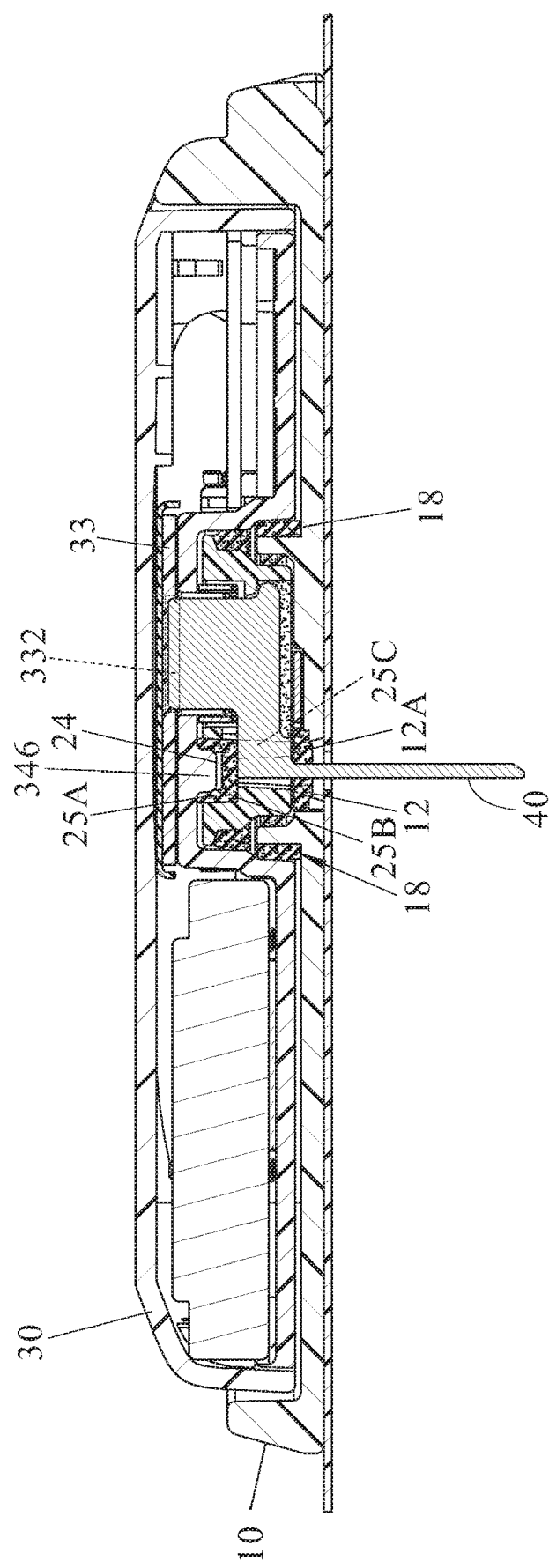
FIG. 3 is a cross-sectional view of FIG. 1 along Line I.
Figure 4:
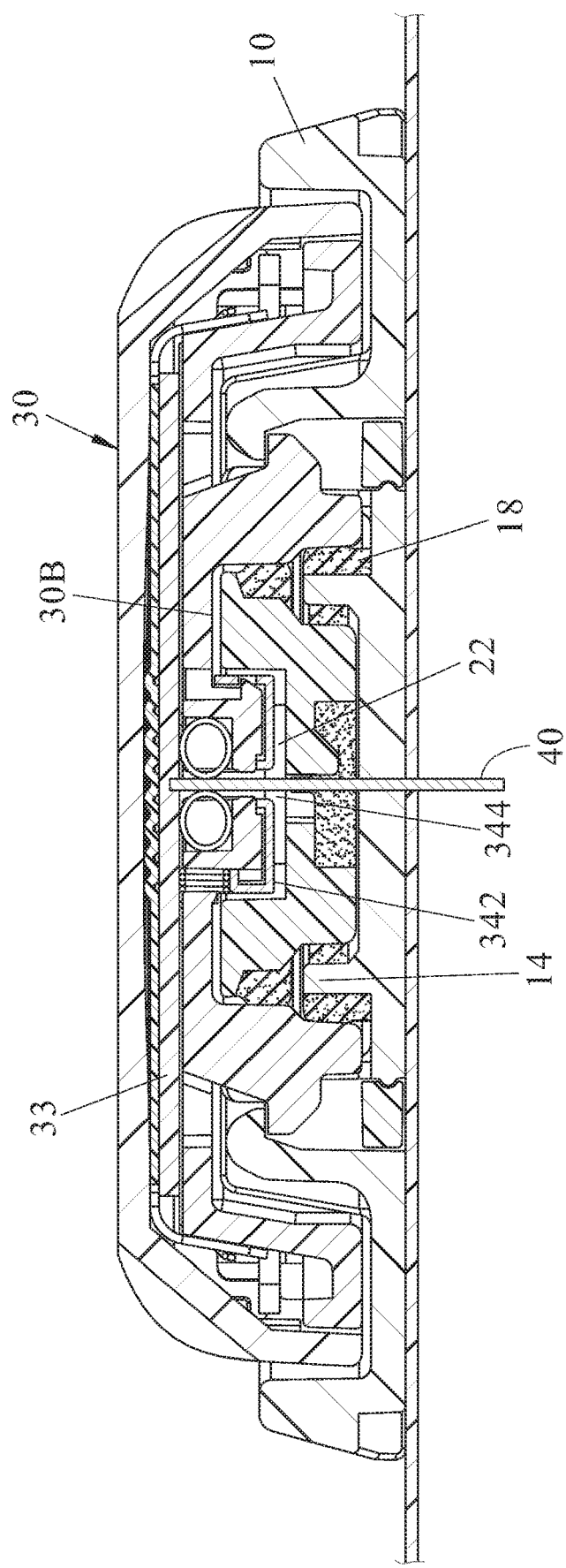
FIG. 4 is a cross-sectional view of FIG. 1 along Line II.

As shown in FIGS. 3 and 4, the port 342 further includes a printed circuit board 33 located in the transmitter 30 and having a recess 332 for containing the top of the sensor 40, so as to reduce the thickness along the assembly direction of the transmitter 30 and the holder 20.

Figure 5A:
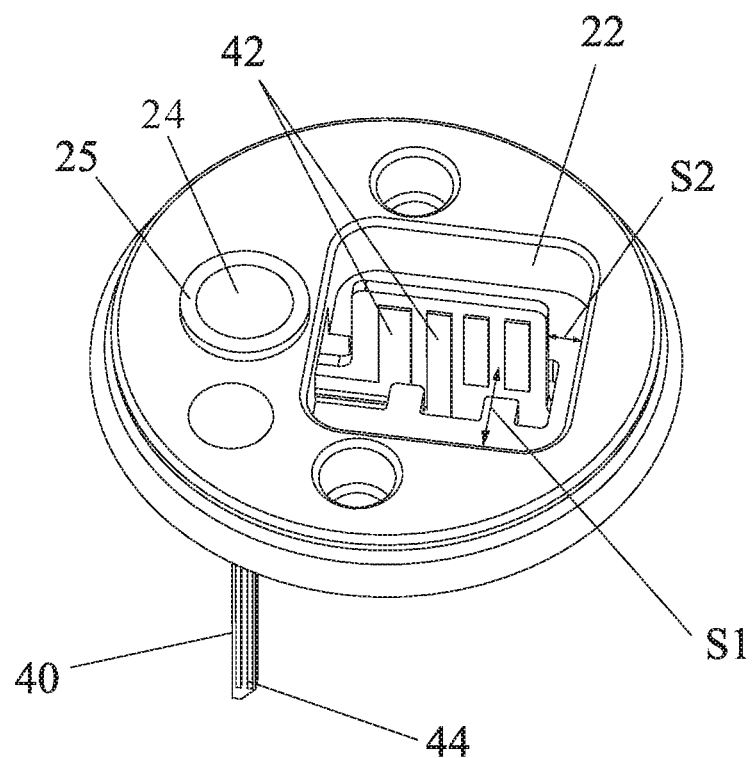
FIG. 5A is a perspective view of the holder of the physiological signal monitoring device in the present invention.
Figure 5B:
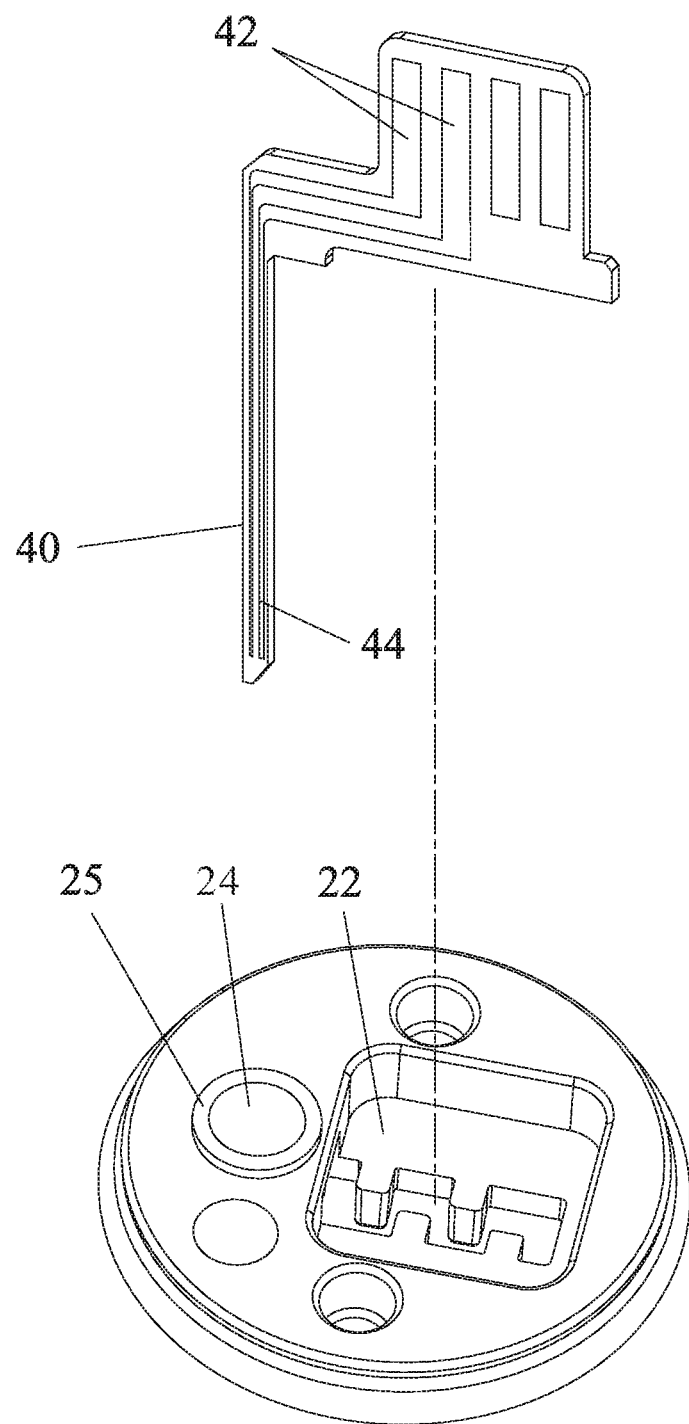
FIG. 5B is an exploded perspective view of FIG. 5A.
Figure 6:
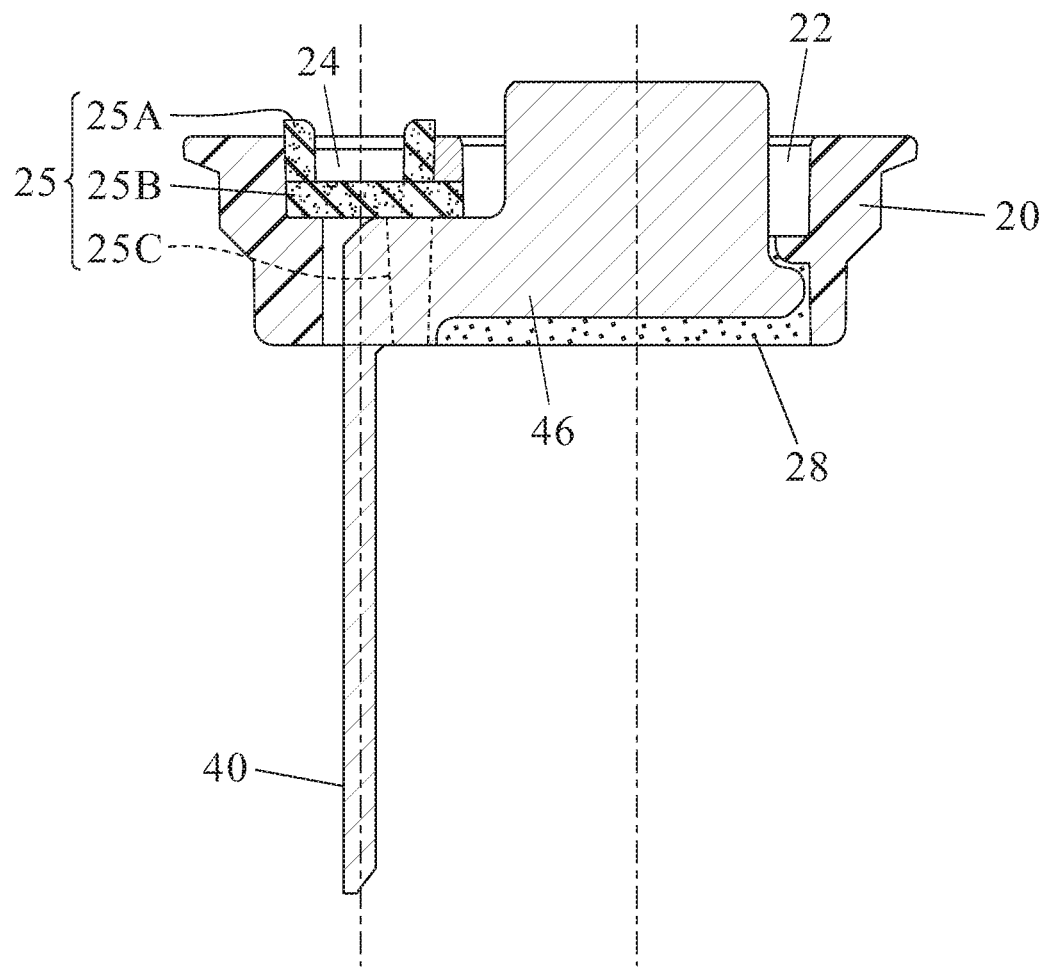
FIG. 6 is a cross-sectional view of FIG. 5A.

Please refer to FIGS. 5A, 5B and 6, which are a perspective view, an exploded perspective view and a cross-sectional view of the holder 20 of the physiological signal monitoring device 1 in the present invention, respectively. The holder 20 has a containing indentation 22 for containing a sensor 40 therein. The sensor 40 is a strip sensor, which has a signal output end 42, a signal detection end 44 and a connecting section 46 connecting the signal output end 42 and the signal detection end 44. The signal output end 42 is disposed on the containing indentation 22 and partially protrudes beyond the containing indentation 22 for electrically connecting to the port 342 of the transmitter 30 and outputting the physiological signal to the transmitter 30. The signal detection end 44 is implanted under the skin of the living body to detect the physiological signal. There are spaces S1 and S2 between the surrounding wall of the containing indentation 22 and the sensor 40 to accommodate the corresponding structure of the transmitter 30. As shown in FIG. 2B and FIG. 4, the lower surface 30B of the transmitter 30 has a first open portion 34, and a port 342 having a connecting slot 344 is provided in the first open portion 34. The port 342 protrudes into the containing indentation 22 of the holder 20 and be contained in the containing indentation 22, so that the sensor 40 is inserted into the connecting slot 344 in the port 342 for electrical connection between the signal output end 42 and the port 342. The port 342 is complementarily accommodated in the space S1 and S2 of the containing indentation 22. With the cooperation of the structure of the sensor 40 and the spatial configuration of the holder 20 as mentioned above, the holder 20 can be adapted to a thin design.

The holder 20 also has a implantation hole 24, wherein the implantation hole 24 corresponds to the through-hole 12 on the base 10 to form an implanting channel. The implanting channel is adapted for the inserting tool (not shown) to extend therethrough, so as to insert the signal detection end 44 under the skin of the living body. The implantation hole 24 penetrates the upper and lower surfaces of the holder 20 and communicates with the containing indentation 22, to contain a part of the sensor 40.

Please refer to FIGS. 3, 6, 7A, 7B and 8, the holder 20 has a fixing indentation 27 for fixing the sensor 40, wherein the fixing indentation 27 communicates with the containing indentation 22, and the implantation hole 24 communicates with the containing indentation 22 through the fixing indentation 27. Since the sensor 40 has turning angles, the signal output end 42 is contained in the containing indentation 22, and the signal detection end 44 extends downward along the axial direction of the implantation hole 24, and thus the sensor 40 penetrates the holder 20. The implantation hole 24 and the containing indentation 22 are respectively configurated on two different longitudinal axes (as shown by dashed axial lines in FIG. 6), so that the signal detection end 44 and the signal output end 42 of the sensor 40 are configured on the longitudinal axes of the implantation hole 24 and the containing indentation 22, respectively.

The holder 20 further has a second elastic body 25 for sealing the implantation hole 24 and fixing the sensor 40. The second elastic body 25 includes a waterproof seal 25A, an elastic divider 25B and a blocking element 25C. The waterproof seal 25A is disposed above the implantation hole 24, preferably at the outer edge of the implantation hole 24, to abut against the transmitter 30 and form therebetween a waterproof sealing structure. The waterproof seal 25A corresponds to a fitting portion 346 of the port 342 of the transmitter 30 (as shown in FIG. 2B), and the fitting portion 346 and the waterproof seal 25A form an interference fit in a complementary manner (as shown in FIG. 3). With a complementary waterproof sealing structure, external liquid is prevented from flowing, from the space between the transmitter 30 and the base 10, and thus affecting the electrical properties of the transmitter 30 and the detection sensitivity of the sensor 40. With the aid of waterproof design above, the user does not need to worry about the influence of external liquid or sweat on the physiological signal monitoring device 1 of the present invention. When the user wears the physiological signal monitoring device 1 of the present invention, he or she can still perform daily activities such as bathing and sports.

The elastic divider 25B is disposed in the implantation hole 24 and corresponds to the space above the implanting channel defined by the implantation hole 24 and the through-hole 12, to separate the implantation hole 24 and covers all over the cross-sectional area of the implantation hole 24. When the inserting tool of the implanting device passes through the elastic divider 25B, drives the signal detection end 44 to be implanted under the skin and is retracted, the design of the elastic divider 25B restores and tightly closes the hole punctured by the inserting tool due to its elasticity. This design avoids blood refluxing through the implanting channel from leaking toward the transmitter 30 and causing visual discomfort to the user.

In order to prevent blood from refluxing through the implanting channel and damaging the electronic components in the transmitter 30, a sealing member 12A disposed on the through-hole 12 of the base 10 and the elastic divider 25B disposed in the implantation hole 24 of the holder 20 are provided in the present invention, to seal the through-hole 12 and the implantation hole 24, respectively. The sealing member 12A and the elastic divider 25B are arranged so that blood effusing from the implantation site of the skin surface of the living body cannot penetrate into the transmitter 30 through the implanting channel above, so as to avoid the electronic components inside the transmitter 30 from being damaged. The material of the sealing member 12A and the elastic divider 25B can be an elastic body (such as rubber), so that it can enclose after the implantation needle is withdrawn and be densely pressed against the signal detection end 44 of the sensor 40 to maintain the seal performance inside the device. Furthermore, the sealing member 12A can also be omitted if the bottom of the holder 20 is sealed by gluing or any form of sealing. In other embodiment, one of the sealing member 12A and the elastic divider 25B can be selected to prevent the blood effusing.

The blocking element 25C is disposed between the implantation hole 24 and the fixing indentation 27 for holding the connecting section 46 of the sensor 40 so as to fix the sensor 40. In the present invention, the material of both of the waterproof seal 25A and the elastic divider 25B is rubber but not limited thereto, it may also be other elastic materials that prevent liquid leakage. The blocking element 25C may be an elastic element or a non-elastic element. In one embodiment, the waterproof seal 25A, the elastic divider 25B and the blocking element 25C are integrally formed and embedded in the implantation hole 24. In other embodiments, the waterproof seal 25A, the elastic divider 25B and the blocking element 25C may be separate elements.

Figure 8:
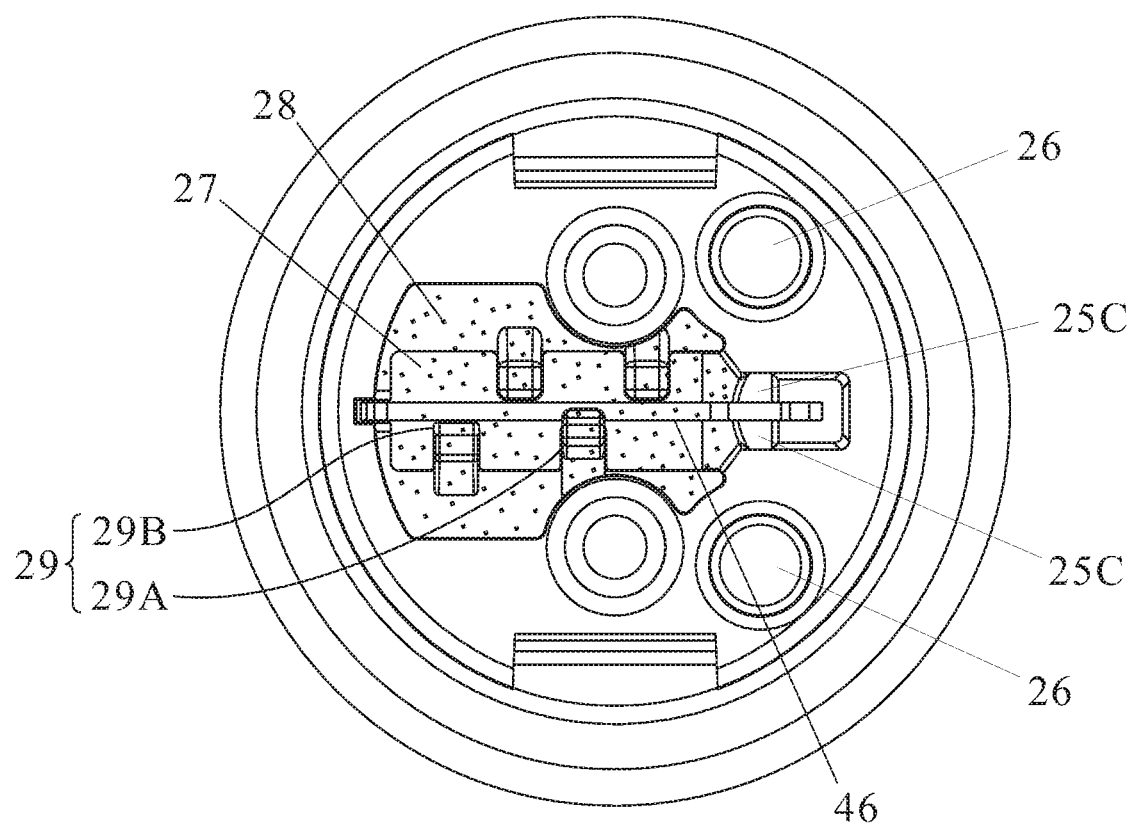
FIG. 8 is a bottom view of the holder of the physiological signal monitoring device in the present invention.

Please refer to FIGS. 7A, 7B and 8. The bottom of the holder 20 is provided with a plurality of limiters 29, which are arranged between the containing indentation 22 and the fixing indentation 27 to restrict the sensor 40. The plurality of limiters 29 may include at least one hook portion 29A and a pressing portion 29B. When the sensor 40 is inserted into the holder 20 from the fixing indentation 27, its signal output end 42 is disposed and protrudes beyond the containing indentation 22, the connecting section 46 connecting the signal detection end 44 is disposed in the fixing indentation 27, and the signal detection end 44 extends through the implantation hole 24. In addition, the hook portion 29A of the limiters 29 is used to limit the connecting portion 46, and the pressing portion 29B of the limiters 29 is used to hold the connecting portion 46. The plurality of limiters 29 of the present invention may be configured alternately or symmetrically without affecting the functions of the hook portion 29A and the pressing portion 29B.

Figure 9:
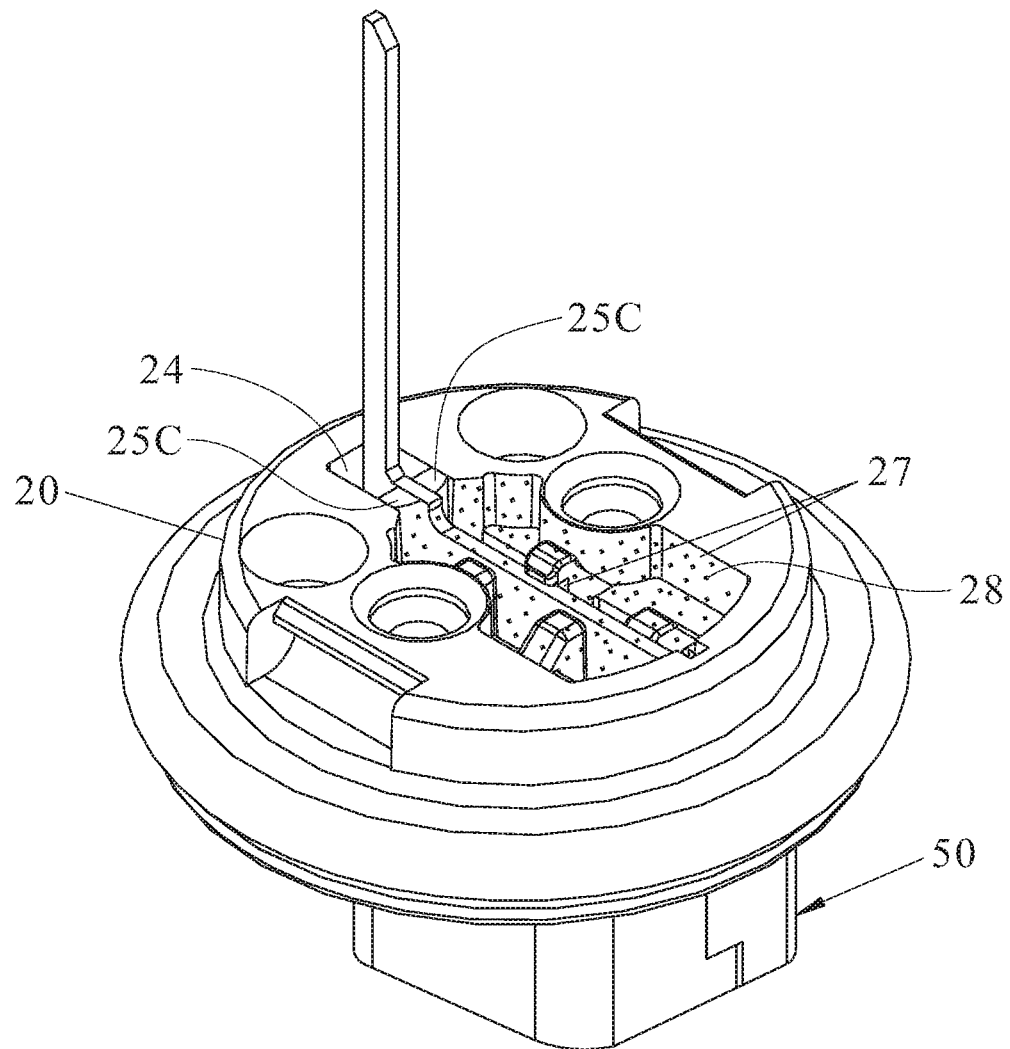
FIG. 9 is an assembly view of the holder and the jig according to a first embodiment.

After fixing the sensor 40 to the holder 20, the bottom of the holder 20 is further sealed. The purposes of waterproofing and fixing the sensor 40 is achieved in the present invention by configuring a filler (i.e. the dotted area as shown in FIGS. 7A, 7B, 8 and 9) in the fixing indentation 27 of the holder 20. According to the first embodiment of the present invention, the bottom of the holder 20 is filled with glue 28. As shown in FIG. 9, a jig 50 with a shape matching the containing indentation 22 is inserted into the containing indentation 22 from the top surface of the holder 20 and clamps the signal output end 42 of the sensor 40, to ensure that the glue 28 does not overflow. The glue 28 is filled into the fixing indentation 27 from the bottom surface of the holder 20. Specifically, the glue 28 can be filled into the whole fixing indentation 27 and blocked by the blocking element 25C without overflowing into the implantation hole 24. However, the degree of sealing can be altered according to the required seal performance and configurations of other components, and the present invention is not limited to the embodiments as described. After the glue 28 is solidified, the jig 50 is removed.

Figure 10A:
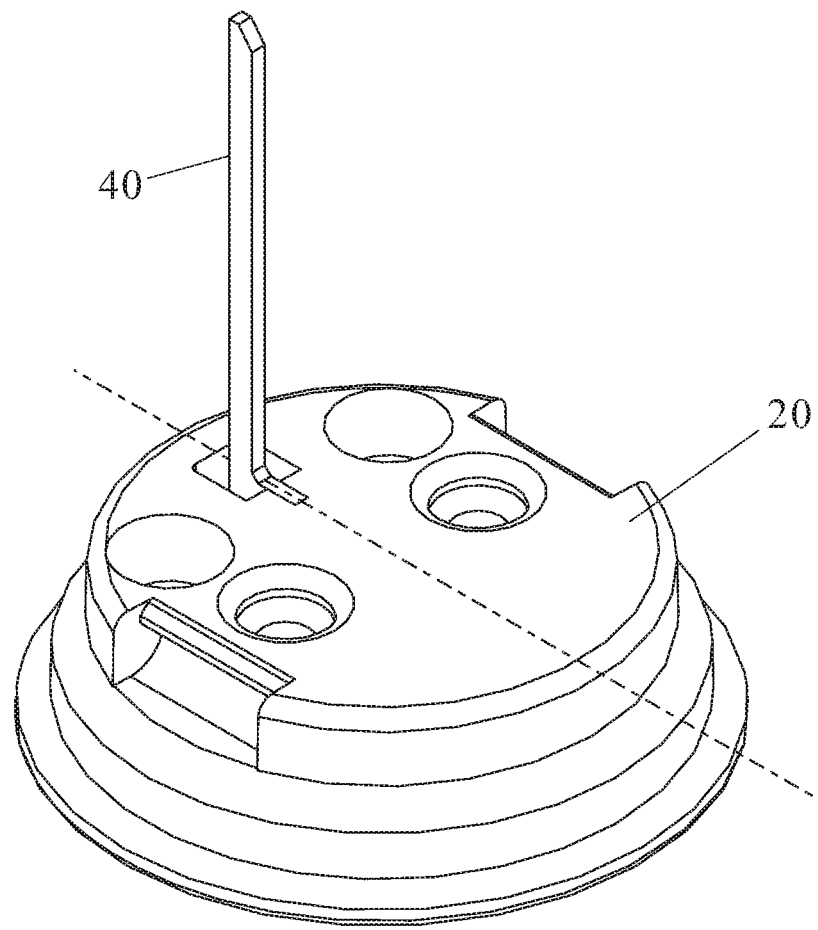
FIGS. 10A and 10B are a perspective view and a cross-sectional view of the holder according to the second embodiment, respectively.
Figure 10B:
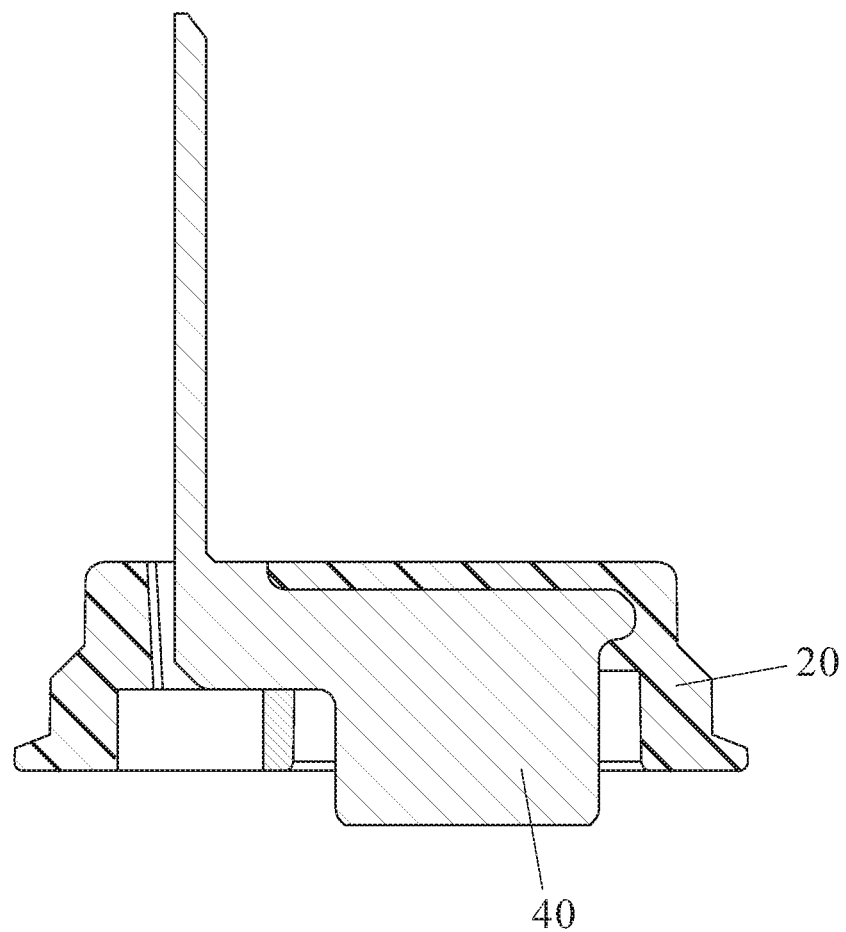

According to the second embodiment of the present invention, the holder 20 is made as one-piece by an insert molding. For example, the holder 20 directly covers the sensor 40 during the insert molding, so as to partially encapsulate the sensor 40 in the holder 20. FIG. 10B shows a cross-sectional view along the dashed line in FIG. 10A. In this embodiment, the limiter 29 and the blocking element 25C can be omitted.

Figure 11A:
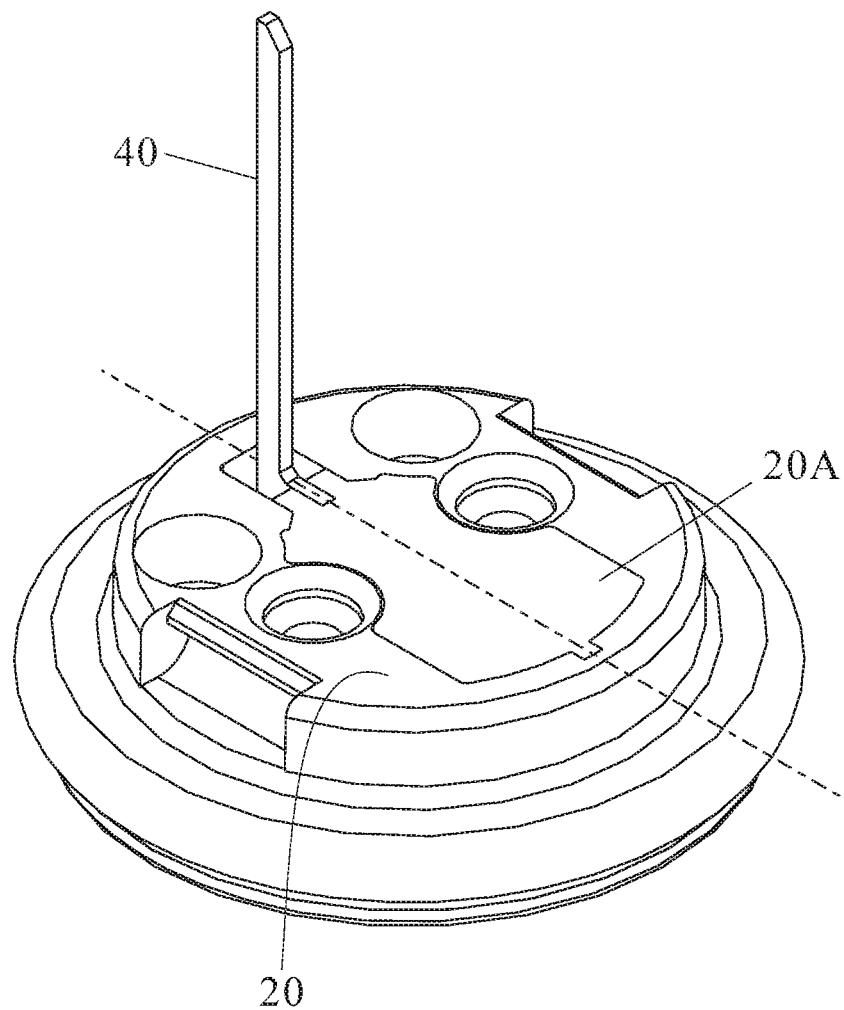
FIGS. 11A and 11B are a perspective view and a cross-sectional view of the holder according to the third embodiment, respectively.
Figure 11B:
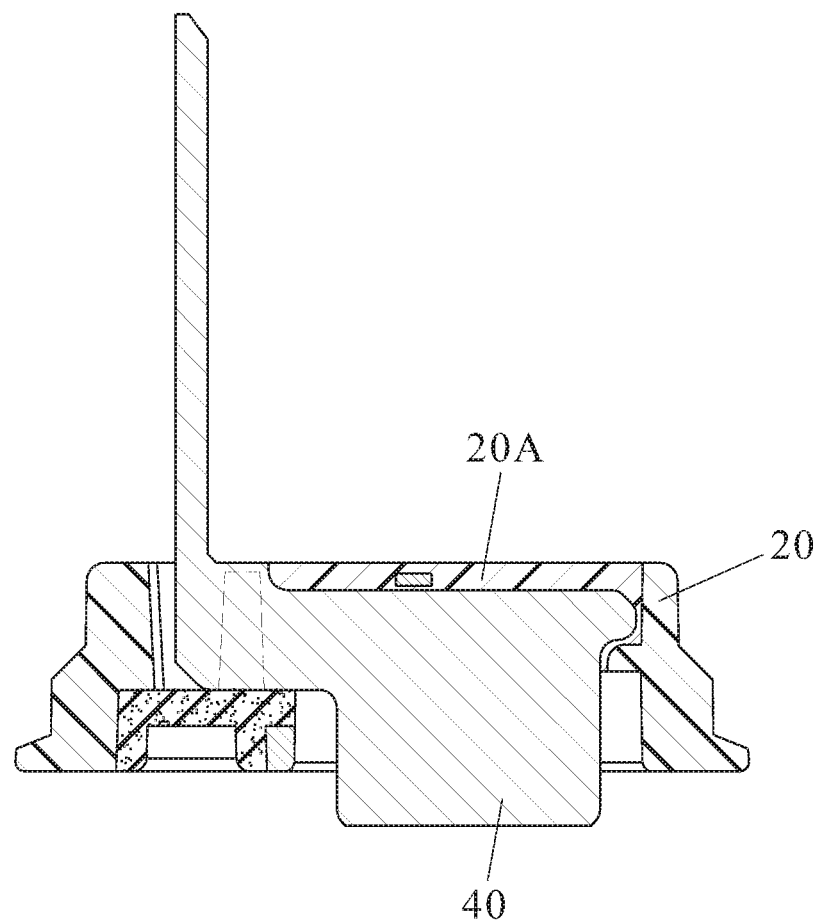

FIG. 11A is a perspective view of the holder according to a third embodiment, and FIG. 11B shows a cross-sectional view along the dashed line in FIG. 11A. According to the third embodiment of the present invention, the bottom of the holder 20 is sealed by filling an inserter 20A rather than glue in the fixing indentation 27 to achieve the effects of sealing the bottom of the holder 20 and holding the sensor 40. Preferably, the inserter 20A is a bottom cap.

Through the detailed description above, it can be understood that the physiological signal monitoring device 1 of the present invention has the following advantages over the prior art:

1. Thin Design

As shown in FIG. 6, in order to match the turning shape of the sensor 40, the implantation hole 24 and the containing indentation 22 of the holder 20 are respectively positioned along two different longitudinal axes and communicate with each other, so that the sensor 40 can be held within the holder 20. With the cooperation of the structure of the sensor 40 and the spatial configuration of the holder 20 as mentioned above, the holder 20 provided in the present invention can be adapted to a thin design.

With regard to the assembly of the transmitter 30 and the holder 20, the port 342 of the transmitter 30 is accommodated in the space S1 of the containing indentation 22 of the holder 20. In addition, the top of the holder 20 is lower than the top of the signal output end 42, thereby the signal output end 42 partially protrudes beyond the holder 20 and is contained in the connecting slot 344 of the port 342 and the recess 332 of the printed circuit board 33 (as shown in FIGS. 3 and 4). The purpose of thinness and detachability is achieved by the above-mentioned complementary structural design.

2. Waterproof Sealing Effect

In the present invention, the second elastic body 25 disposed in the implantation hole 24 of the holder 20 includes the waterproof seal 25A and the elastic divider 25B. The waterproof seal 25A abuts against the transmitter 30 to form therebetween a waterproof sealing structure, to prevent external liquid from flowing into the space between the transmitter 30 and the base 10 and affecting the electrical properties of the transmitter 30 and the detection sensitivity of the sensor 40. The elastic divider 25B is disposed in the implantation hole 24 and corresponds to the space above the implanting channel defined by the implantation hole 24 and the through-hole 12, to prevent blood refluxing through the implanting channel from leaking toward the transmitter 30.

3. Fixing Effect for the Sensor

The holder 20 of the present invention is used to carry the sensor 40 through the filler filling the fixing indentation 27 and the limiters 29 arranged between the containing indentation 22 and the fixing indentation 27. In addition, the blocking element 25C of the second elastic body 25 holds the connecting section 46 of the sensor 40 so as to fix the sensor 40. Therefore, the present invention enables the sensor 40 to be more stably carried on the holder 20 through the limiting and fixing means of the filler, the limiter 29 and the blocking element 25C.

What is claimed is:

1. A physiological signal monitoring device for implantation under a skin of a living body to measure a physiological signal of an analyte in a biological fluid from the living body, comprising:

a sensor having a signal detection end and a signal output end, wherein the signal detection end is to be implanted under the skin to detect the physiological signal, and the signal output end is to output the physiological signal;

a transmitter having a port connected to the signal output end and receiving the physiological signal, wherein the port comprises a connecting slot; and a holder carrying thereon the sensor, the holder having a top positioned lower than a top of the signal output end such that the signal output end protrudes beyond the holder and is held within the connecting slot, and the holder comprising:

an implantation hole being a channel for implanting therethrough the sensor, and containing a part of the sensor; and a containing indentation containing the signal output end, wherein the containing indentation has a surrounding wall kept apart from the signal output end to define a space such that the port is received within the space of the containing indentation, and the signal output end is electrically connected to the port.

2. The physiological signal measuring device as claimed in claim 1, further comprising a base, wherein the holder comprises two positioning holes, and the base comprises two positioning pillars contained in the two positioning holes.

3. The physiological signal measuring device as claimed in claim 1, wherein the holder further comprises a waterproof seal disposed above the implantation hole and abutting against the transmitter to form therebetween a waterproof sealing structure.

4. The physiological signal measuring device as claimed in claim 1, wherein the holder further comprises an elastic divider disposed in the implantation hole to separate the implantation hole and covering all over a cross-sectional area of the implantation hole.

5. The physiological signal measuring device as claimed in claim 4, wherein the elastic divider is disposed above the sensor in the implantation hole.

6. The physiological signal measuring device as claimed in claim 1, wherein the holder comprises a limiter for restricting the sensor.

7. The physiological signal measuring device as claimed in claim 6, wherein the limiter comprises a hook portion or a pressing portion.

8. The physiological signal measuring device as claimed in claim 1, wherein the implantation hole and the containing indentation are respectively positioned along two different longitudinal axes.

* * * * *